(12) United States Patent
Eckert et al.

(10) Patent No.: US 8,951,616 B2
(45) Date of Patent: Feb. 10, 2015

(54) ESTER GROUP CONTAINING LIQUID CRYSTALS FOR OPTICAL OR ELECTRO OPTICAL DEVICES

(75) Inventors: Jean Francois Eckert, Kientzville (FR); Martin Roth, Holstein (CH)

(73) Assignee: Rolic AG, Zug (CH)

( * ) Notice: Subject to any disclaimer, the term of this patent is extended or adjusted under 35 U.S.C. 154(b) by 180 days.

(21) Appl. No.: 13/382,455

(22) PCT Filed: Jul. 5, 2010

(86) PCT No.: PCT/EP2010/059528
§ 371 (c)(1),
(2), (4) Date: Jan. 5, 2012

(87) PCT Pub. No.: WO2011/003846
PCT Pub. Date: Jan. 13, 2011

(65) Prior Publication Data
US 2012/0114907 A1    May 10, 2012

(30) Foreign Application Priority Data

Jul. 9, 2009  (EP) .................................. 09164992
Jan. 25, 2010  (EP) .................................. 10151538

(51) Int. Cl.
| C09K 19/20 | (2006.01) |
| C07C 69/78 | (2006.01) |
| C09K 19/38 | (2006.01) |
| C09K 19/46 | (2006.01) |
| C09K 19/04 | (2006.01) |

(52) U.S. Cl.
CPC ............ C09K 19/2007 (2013.01); C09K 19/46 (2013.01); *C09K 2019/0448* (2013.01); *C09K 2219/03* (2013.01)
USPC ............ 428/1.1; 252/299.67; 560/85; 560/95

(58) Field of Classification Search
CPC ........... C09K 19/2007; C09K 19/2014; C09K 19/22; C09K 19/24; C09K 2019/0448; C09K 2219/03; C07C 69/78; C07C 69/80
USPC ............... 252/299.5, 299.64, 299.65, 299.67, 252/299.01; 560/76, 85, 95; 349/117; 428/1.1
See application file for complete search history.

(56) References Cited

U.S. PATENT DOCUMENTS

| 5,539,074 A | 7/1996 | Herr et al. |
| 5,593,617 A | 1/1997 | Kelly et al. |
| 5,650,534 A | 7/1997 | Kelly et al. |
| 5,700,393 A | 12/1997 | Kelly |
| 5,798,147 A | 8/1998 | Beck et al. |
| 5,851,424 A | 12/1998 | Kelly |
| 6,107,427 A | 8/2000 | Herr et al. |
| 6,201,087 B1 | 3/2001 | Herr et al. |
| 6,395,351 B1 | 5/2002 | Benecke et al. |
| 6,548,127 B1 | 4/2003 | Benecke et al. |
| 6,613,245 B1 | 9/2003 | Ohlemacher et al. |
| 6,630,076 B1 | 10/2003 | Cherkaoui et al. |
| 6,676,851 B1 | 1/2004 | Buchecker et al. |
| 6,733,690 B1 | 5/2004 | Lukac et al. |
| 6,746,729 B1 | 6/2004 | Cherkaoui et al. |
| 6,749,771 B1 | 6/2004 | Cherkaoui et al. |
| 7,364,671 B2 | 4/2008 | Schadt et al. |
| 2003/0168633 A1 | 9/2003 | Wellinghoff et al. |
| 2003/0219548 A1 | 11/2003 | Meyer et al. |
| 2004/0164272 A1 | 8/2004 | Buckecker et al. |
| 2005/0040364 A1 | 2/2005 | Cherkaoui et al. |
| 2006/0049381 A1 | 3/2006 | Klein et al. |
| 2006/0188663 A1 | 8/2006 | Peglow et al. |
| 2007/0257230 A1 | 11/2007 | Cherkaoui et al. |
| 2008/0001120 A1 | 1/2008 | Peglow et al. |

FOREIGN PATENT DOCUMENTS

| EP | 0 611 786 A1 | 8/1994 |
| EP | 0 763 552 A2 | 3/1997 |
| JP | 11-080090 A | 3/1999 |
| JP | 11-80090 A | 3/1999 |
| WO | WO 95/24455 A1 | 9/1995 |
| WO | WO 96/10049 A1 | 4/1996 |
| WO | WO 99/37735 A1 | 7/1999 |
| WO | WO 99/64924 A1 | 12/1999 |
| WO | WO 00/04110 A1 | 1/2000 |
| WO | WO 00/05189 A1 | 2/2000 |
| WO | WO 00/07975 A1 | 2/2000 |
| WO | WO 00/48985 A1 | 8/2000 |
| WO | WO 03/027056 A1 | 4/2003 |
| WO | WO 2004/085547 A1 | 10/2004 |
| WO | WO 2005/054406 A1 | 6/2005 |
| WO | WO 2005/105932 A1 | 11/2005 |

OTHER PUBLICATIONS

English translation by computer for JP 1180090 (1999), http://www4.ipdl. inpit.go.jp/Tokujitu/PAJdetail.ipdl?N0000=60&N0120=01&N2001=2&N3001=H11-080090.*

* cited by examiner

*Primary Examiner* — Shean C Wu
(74) *Attorney, Agent, or Firm* — Sughrue Mion. PLLC

(57) ABSTRACT

The invention relates to polymerizable liquid crystals compound (I) having a liquid crystalline phase and to liquid crystalline compositions comprising compounds (I), their use as birefringence layer.

12 Claims, No Drawings

ESTER GROUP CONTAINING LIQUID CRYSTALS FOR OPTICAL OR ELECTRO OPTICAL DEVICES

CROSS REFERENCE TO RELATED APPLICATIONS

This application is a National Stage of International Application No. PCT/EP2010/059528 filed Jul. 5, 2010, claiming priority based on European Patent Application Nos. 09164992.1, filed Jul. 9, 2009 and 10151538.5, filed Jan. 25, 2010, the contents of all of which are incorporated herein by reference in their entirety.

The invention relates to polymerisable liquid crystal compounds (I) and their compositions and polymers, which are used for the preparation of birefringent layers for optical or electro optical devices.

Birefringent layers are used in the manufacture of optical or electro optical components such as waveguides, optical gratings, filters, retarders, rotators, piezoelectric cells and non-linear optical cells and films. The choice of liquid crystal compounds for use in any one of the aforementioned optical or electro optical components depends upon its associated optical properties such as the optical anisotropy, refractive index, transparency and dispersion.

Birefringent layers can for example be manufactured by orientating a layer comprising a liquid crystal compound.

The configuration imposed by an orientation layer on a liquid crystal compound can be stabilised if the liquid crystal is polymerisable, and herewith gives access to fix the orientation by forming a polymer network. The resulting birefringent layer has a high viscosity and is stable to mechanical stresses, temperature and light exposure.

Desired are polymerisable liquid crystal compounds, which are stable against chemical, thermal influences or electromagnetic radiation. Further, good manufacturing properties deriving from polymerisable liquid crystal compounds are desired, such as easy and economic accessibility. In addition, of advantage are polymerisable liquid crystal compounds having good applicatory properties such as good adhesion, solubility and miscibility with other polymerisable liquid crystal compounds, and extended liquid crystalline phase(s) over a large temperature range such as from 25 to 80° C., more advantageously 25 to 150° C.

There is a need for further polymerisable liquid crystal compounds which exhibits a broad liquid-crystalline thermal range and which can be orientated on a substrate, preferably prior to cross-linking in such a way that the orientation of the polymerisable liquid crystal compounds or mixture on the substrate remains stable over the period required for manufacturing the polymer network. Further, these polymerisable liquid crystal compounds should economically be accessible and show good applicatory properties.

The present invention relates to a polymerisable liquid crystal compound (I) having a liquid crystalline phase:

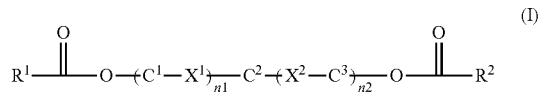
(I)

wherein $R^1$ and $R^2$ are independently from each other a group of formula (Ia)

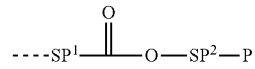
(Ia)

wherein:
"- - - -", the interrupted line, symbolizes the linkage to compound (I), and wherein
—$(C^1-X^1)n^1-C^2-(X^2-C^3)n^2$- is a divalent core, wherein;
$C^1$ and $C^3$ are in each case independently substituted or unsubstituted non-aromatic, aromatic, carbocyclic or heterocyclic groups, and
$C^2$ is a nonaromatic, aromatic, carbocyclic or heterocyclic group which is unsubstituted or substituted with an unbranched hydrocarbon group of 1 to 20 C-atoms, wherein one or more C-atom, —CH— or —CH$_2$-group, is not replaced or, in which one or more C-atom, —CH— or —CH$_2$-group, is replaced by a heteroatom, such as —O—, —S—, —NH—, —N(CH$_3$)—, or is replaced by a replacing-group selected from the group consisting of —N=N—, —CO—C=C—, —CH(OH)—, —CO—, —SO—, —CH$_2$(SO)—, —SO$_2$—, —CH$_2$(SO$_2$)—, —COO—, —O(CO)—, —O(CO)—O—, —S—CO—, —CO—S—, —SOO—, —OSO—, —CH=CH— and —C≡C— with the proviso that oxygen atoms are not directly linked to each other;
$X^1$ and $X^2$ each independently represent —O—, —S—, —NH—, —N(CH$_3$)—, —N=N—, —CH=N—, —N=CH—, —CO—C=C—, —CH(OH)—, —CO—, —CH$_2$O—, —OCH$_2$—, —CH$_2$(CO)—, —SO—, —CH$_2$(SO)—, —SO$_2$—, —CH$_2$(SO$_2$)—, —OCF$_2$—, —COO—, —O(CO)—, —O(CO)—O—, —S—CO—, —CO—S—, —SOO—, —OSO—, —CH$_2$—CH$_2$—, —CH$_2$—CH$_2$—CH$_2$—CH$_2$—, —OCH$_2$—, —CH$_2$O—, —CH=CH—, —C≡C— or a single bond;
$n^1$ and $n^2$ are integers, each independently having a value from 0, 1, 2, 3, 4, preferably 1,
$SP^1$ represents a nonaromatic or aromatic, carbocyclic or heterocyclic group, or a CH=CH-group, C≡C-group or a branched or unbranched $C_3$-$C_{24}$-alkylen group, wherein one or more C-atom, —CH— or —CH$_2$-group, is not replaced, or, in which one or more C-atom, —CH— or —CH$_2$-group, is replaced by a heteroatom or at least a single replacing-group selected from the group consisting of —N=N—, —CO—C=C—, CO—, —CH$_2$(CO)—, —SO—, —CH$_2$(SO)—, —SO$_2$—, —CH$_2$(SO$_2$)—, —COO—, —O(CO)—, —O(CO)—O—, —S—CO—, —CO—S—, —SOO—, —OSO—, —OCH$_2$—, —CH$_2$O—, —CH=CH— and —C≡C—; with the proviso that oxygen atoms are not directly linked to each other;
more preferably $SP^1$ represents a CH=CH-group (cis or trans), C≡C-group or substituted or unsubstituted $C_3$-$C_{12}$alkylen, most preferably $C_3$-$C_6$alkylen, especially n-propylene, n-butylen, n-pentylen, n-hexylen, wherein one or more C-atom, —CH— or —CH$_2$-group, is not replaced, or, in which one or more C-atom, —CH— or —CH$_2$-group, is replaced by —O— or —S—, or at least a single CH=CH-group (cis or trans); with the proviso that oxygen atoms are not directly linked to each other;
$SP^2$ represents a substituted or unsubstituted spacer;
preferably $SP^2$ represents a nonaromatic or aromatic, carbocyclic or heterocyclic group, or branched or unbranched $C_1$-$C_{24}$-alkylen group, wherein one or more C-atom, —CH— or —CH$_2$-group, is not replaced, or, in which one or more C-atom, —CH— or —CH$_2$-group, is replaced by a heteroatom or at least by a single replacing-group selected from the group consisting of —N=N—, —CO—C=C—, CO—, —CH$_2$(CO)—, —SO—, —CH$_2$(SO)—, —SO$_2$—, —CH$_2$(SO$_2$)—, —COO—, —O(CO)—, —O(CO)—O—, —S—CO—, —CO—S—, —SOO—, —OSO—, OCH$_2$—, —CH$_2$O—, —CH=CH— and —C≡C—; with the proviso that oxygen atoms are not directly linked to each other;

more preferably SP$^2$ represents substituted or unsubstituted C$_1$-C$_{12}$alkylen, most preferably C$_1$-C$_6$alkylen, especially methylen, ethylene, n-propylene, n-butylen, n-pentylen, n-hexylen, wherein one or more C-atom, —CH— or —CH$_2$- group, is not replaced, or, in which one or more C-atom, —CH— or —CH$_2$-group, is replaced by a heteroatom or at least a single by a replacing-group selected from the group consisting of —N=N—, —CO—C=C—, CO—, —CH$_2$(CO)—, —SO—, —CH$_2$(SO)—, —SO$_2$—, —CH$_2$(SO$_2$)—, —COO—, —O(CO)—, —O(CO)—O—, —CO—S—, —SOO—, —OSO—, OCH$_2$—, —CH$_2$O—, —CH=CH— and —C≡C—; with the proviso that oxygen atoms are not directly linked to each other;

especially most preferably SP$^2$ represents unsubstituted C$_1$-C$_6$alkylene, methylene, ethylene, n-propylene, n-butylen, n-pentylen, n-hexylen, wherein one or more C-atom, —CH— or —CH$_2$-group, is not replaced, or, in which one or more C-atom, —CH— or —CH$_2$-group, is replaced by —O— or —S—, or at least a single CH=CH-group; with the proviso that oxygen atoms are not directly linked to each other;

P is a polymerizable group.

Further preferred is compound (I) wherein SP$^1$ and —SP$^2$ are different from each other.

In the context of the present invention halogen has the meaning of fluoride, chloride, bromide and iodide, preferably of fluoride and chloride;

—CH=CH— has the meaning of the corresponding cis or trans group;

substituent(s) are preferably halogen, aryl, cycloalkyl, amino, cyano, epoxy, hydroxy, nitro, oxo, alkyl, alkoxy, C$_1$-C$_{20}$-alkoxycarbonyl, alkylcarbonyloxy, alkylcarbonyl, alkylcarbonylamino;

the term alkyl used as a single term or in combined words or in combination with other terms is for example C$_1$-C$_{24}$alkyl, preferably C$_1$-C$_{10}$alkyl, more preferably C$_1$-C$_6$alkyl, which is substituted, unsubstituted, branched, unbranched, unreplaced or in which one or more C-atoms may be replaced by heteroatom, such as —O—, —S—, —N(CH$_3$)—, or replacing-groups selected from the group consisting of —N=N—, —CO—C=C—, —CO—, —CH$_2$(CO)—, —SO—, —CH$_2$(SO)—, —SO$_2$—, —CH$_2$(SO$_2$)—, —COO—, —O(CO)—, —O(CO)—O—, —S—CO—, —CO—S—, —SOO—, —OSO—, —CH$_2$—CH$_2$—, —OCH$_2$—, —CH$_2$O—, —CH=CH—, —C≡C— and a single bond; preferred is methyl, ethyl, propyl, isopropyl, n-butyl, iso-butyl, isopentyl, n-pentyl, n-hexyl, iso-hexyl, or is replaced by —O—, —COO—, —OCO—;

the term alkylene is the biradical derivative of alkyl, wherein alkyl has the above-described meanings and preferences;

the term alkoxy is the —O-alkyl derivate, the term alkoxycarbonyl is the —COO-alkyl derivate, the term alkylcarbonyloxy is the —OCO-alkyl derivate, the term alkylcarbonyl is the OC-alkyl derivate, the term alkylcarbonylamino is the —HNOC-alkyl derivate, wherein alkyl has the above given meanings and preferences;

the term aryl is the residue of an aromatic group;

the term cycloalkyl is the residue of an non-aromatic, carbocyclic or heterocyclic group;

the term hydrocarbon includes straight-chain and branched alkyl, alkylene, alkenyl, alkenylene, alkenyl, alkinylene;

the term nonaromatic includes carbocyclic or heterocyclic groups the term aromatic includes carbocyclic or heterocyclic groups, which are monocyclic, two adjacent monocyclic rings of five or six atoms, a bicyclic ring system of eight, nine or ten atoms, or a tricyclic ring system of thirteen or fourteen atoms; preferably, the term "aromatic", denotes incorporating five, six, ten or 14 ring atoms, e.g. furan, benzene or phenylene, pyridine, triazine, pyrimidine, naphthalene, phenanthrene, biphenylene or triphenylene, or tetraline units which are uninterrupted or interrupted by at least a single heteroatom and/or at least a single bridging group; preferred aromatic group are benzene, phenylene, biphenylene or triphenylen and most preferably phenylene; preferably the aromatic, carbocyclic or heterocyclic group is for example unsubstituted or mono- or poly-substituted; preferred substituents of carbocyclic or heterocyclic aromatic groups are at least one polar group and/or an alkyl, acryloyloxy, alkylacryloyloxy, alkoxy, alkylcarbonyloxy, alkyloxycarbonyloxy, alkyloxocarbonyloxy, methacryloyloxy, vinyl, vinyloxy and/or allyloxy group; preferred polar groups are nitro, halogen, hydroxyl; cyano or a carboxy group;

the term phenylene or phenyl, as used in the context of the present invention, preferably denotes a 1,2-, 1,3- or 1,4-phenylene or phenyl groups, which are optionally substituted. It is preferred that the phenylene group is either a 1,3- or a 1,4-phenyl(ene) group. 1,4-phenyl(ene) groups are especially preferred.

Preferably, C$^1$ and C$^3$ are selected from:

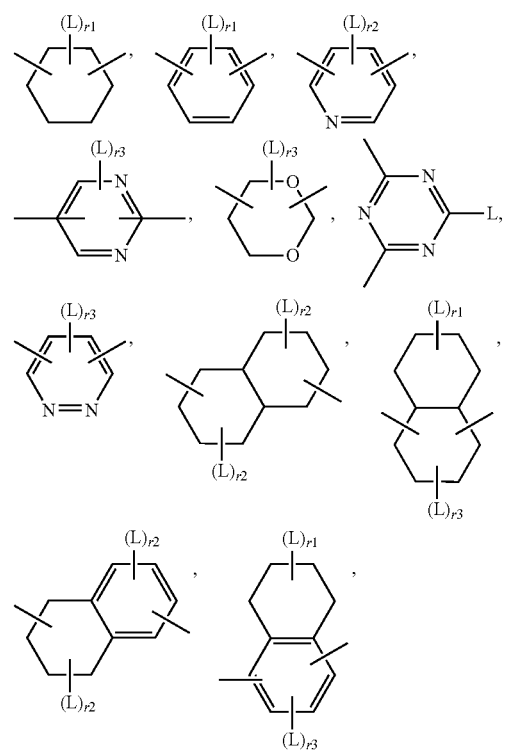

-continued

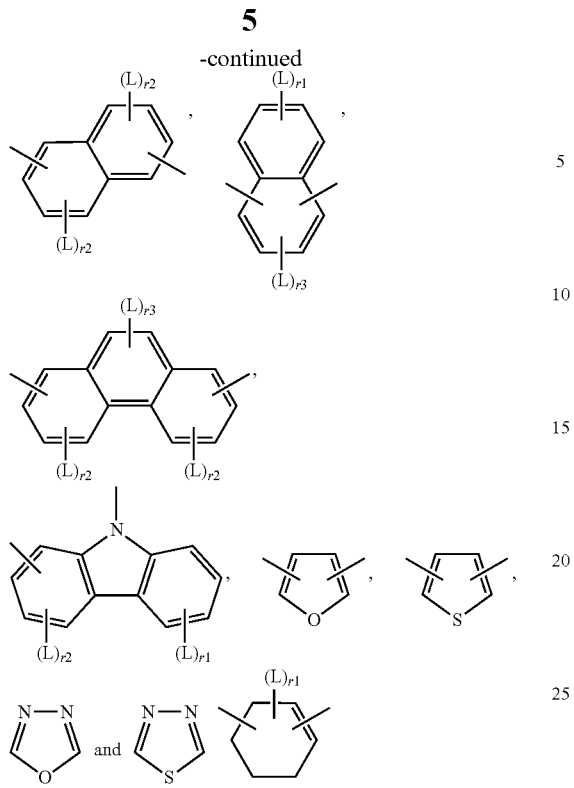

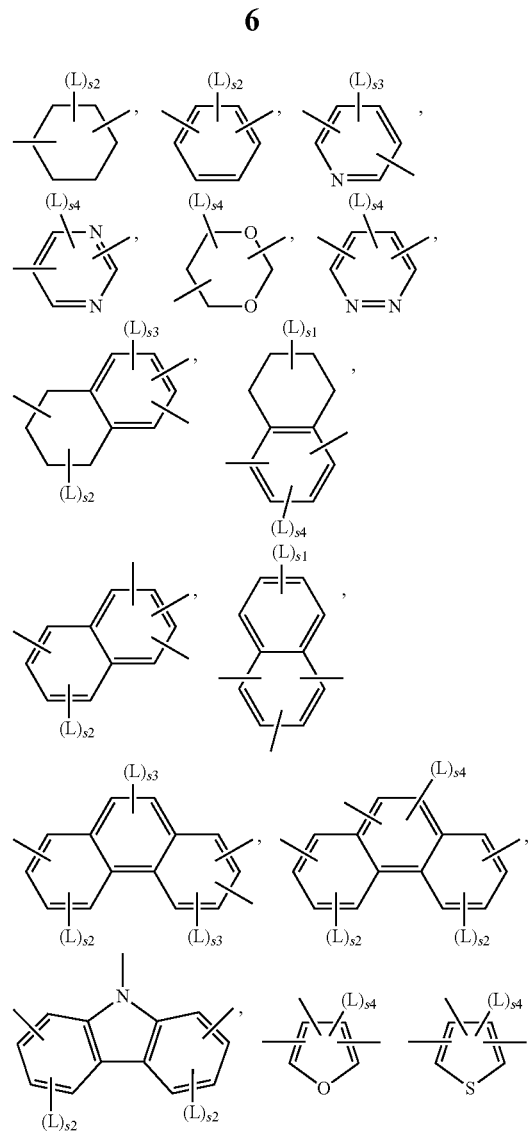

wherein:
L represents hydrogen, halogen, $C_1$-$C_{24}$-alkyl, preferably methyl, ethyl, n-butyl, n-hexyl; $C_1$-$C_{24}$-alkoxy, $C_1$-$C_{24}$-alkoxycarbonyl, $C_1$-$C_{24}$-alkylcarbonyloxy, $C_1$-$C_{24}$-alkylcarbonyl, preferably —COCH$_3$; cyano, $C_1$-$C_{24}$-alkylcarbonylamino; or —NO$_2$,
$r^1$ being 0, 1, 2, 3, or 4,
$r^2$ being 0, 1, 2, or 3, and
$r^3$ being 0, 1, or 2.

More preferably $C^1$ and $C^3$ are selected from the group of compounds consisting of and the chiral groups $C^{2''}$ of compounds shown below:

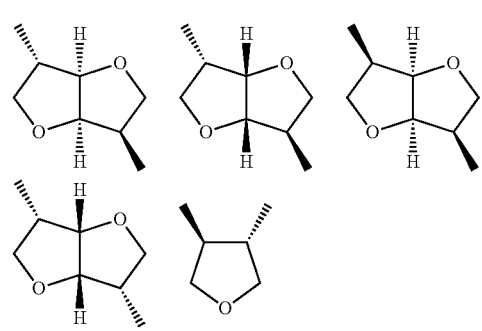

wherein
L represents hydrogen, halogen, methyl, ethyl, propyl, butyl, pentyl, hexyl; $C_1$-$C_6$-alkoxy, —COCH$_3$ nitrile or —NO$_2$, $r^1$, $r^2$ and $r^3$ being independently from each other 0 or 1.

Preferably, $C^2$ is selected from the achiral groups $C^{2'}$ of compounds shown below:

wherein:
L represents hydrogen, unbranched hydrocarbon group of 1 to 6 C-atoms, wherein one or more C-atom, —CH— or —CH$_2$-group, is not replaced, or, in which one or more C-atom, —CH— or —CH$_2$-group, is replaced by a heteroatom, which is —O—, —S—, —NH—, —N(CH$_3$)—, or is replaced by a replacing-group selected from the group consisting of —N=N—, —CO—C=C—, —CH(OH)—, —CO—, —SO—, —CH$_2$(SO)—, —SO$_2$—, —CH$_2$(SO$_2$)—, —COO—, —O(CO)—, —O(CO)—O—, —S—CO—, —CO—S—, —SOO—, —OSO—, —CH=CH— and —C≡C—, with the proviso that oxygen atoms are not directly linked to each other; preferably in which one or more C-atom, —CH— or —CH$_2$-group is not replaced, or is replaced by a —O—, or —COO—, —O(CO)—, —O(CO)—O; more preferably L is hydrogen, methyl, ethyl, propyl, methoxy and most preferably hydrogen or methyl, ethyl or methoxy, and especially most preferred hydrogen or methyl;

$s^1$ being 0, 1, 2, 3, or 4, $s^2$ being 0, 1, 2, or 3, $s^3$ being 0, 1, or 2 and $s^4$ being 0 or 1; and preferably $s^1$, $s^2$ and $s^4$ being independently from each other 0 or 1.

More preferably $C^2$ is selected from the achiral groups $C^{2'}$ of compounds shown below:

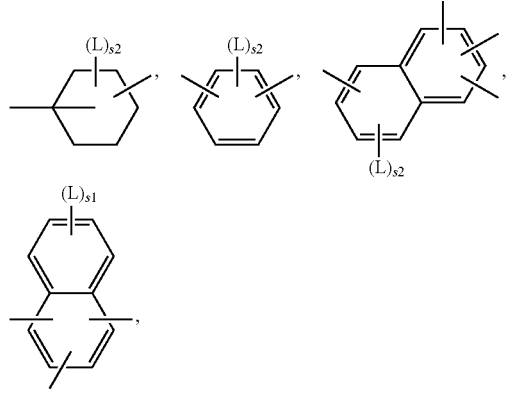

and the chiral groups $C^{2''}$ of compounds shown below:

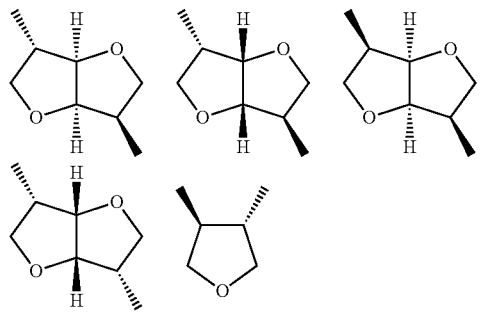

wherein L, $s^1$ and $s^2$ have the same meanings and preferences described above.

Most preferably $C^2$ is selected from the achiral groups $C^{2'}$ of compounds shown below:

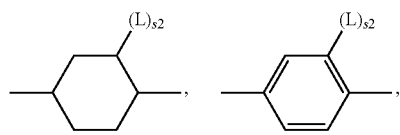

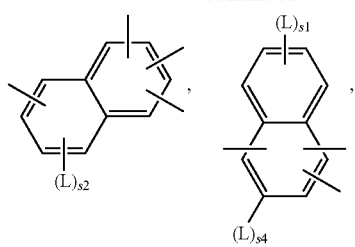

and the chiral groups $C^{2''}$ shown below:

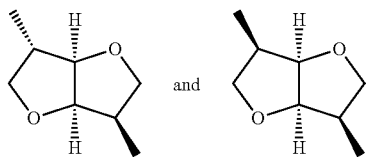

wherein L, $s^1$, $s^2$ and $s^4$ have the same meanings and preferences described above.

Further, more preferred is a compound (I), wherein P is CH$_2$=CZ$^1$—COO—,

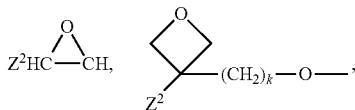

wherein k is an integer from 1 to 20; or

P is HO—CZ$^2$Z$^3$—, HS—CZ$^2$Z$^3$, HZ$^2$N—, CH$_2$=CZ$^1$—CO—NH—,

CH$_2$=CZ$^2$—(O)$_{k1}$—, wherein k1 is 0 or 1; CH$_3$—CH=CH—O—, (CH$_2$=CH)$_2$CH—COO—, (CH$_2$=CH—CH$_2$)$_2$CH—OCO, (CH$_2$=CH)$_2$CH—O—, (CH$_2$=CH—CH$_2$)$_2$N—, (CH$_2$=CH—CH$_2$)$_2$N—CO— or Z$^4$Z$^5$Z$^6$Si—, wherein Z$^1$ is H, Cl, CN, phenyl or C$_1$-C$_6$alkyl, Z$^2$ and Z$^3$ each independently being H or C$_1$-C$_6$alkyl, Z$^4$, Z$^5$ and Z$^6$ each independently being Cl, oxaalkyl or oxacarbonylalkyl with 1 to 6 C-atoms.

Preferably P is CH$_2$=CZ$^1$—COO—

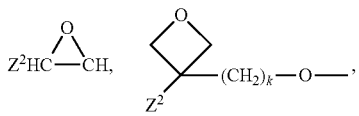

wherein Z$^1$ and Z$^2$ are independently from each other H or C$_1$-C$_6$alkyl, preferably H or methyl and K is an integer from 1 to 6, preferably 1.

More preferably P is CH$_2$=CZ$^1$—COO— wherein Z$^1$ is H, or C$_1$-C$_6$alkyl, which is especially methyl.

In addition, more preferred is a compound of formula (II):

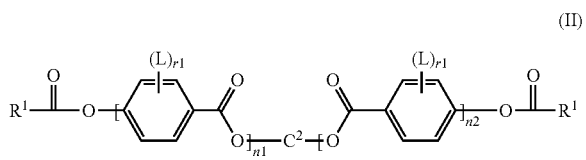

wherein $C^2$, $R^1$, L, $r^1$, $n^1$, $n^2$ have the meanings and preferences as given above; and especially more preferred is compound (II), wherein
$C^2$ is 1,4:3,6-dianhydro-2,5-dideoxy-2,5-dimethyl-D-mannitol, 1,4:3,6-dianhydro-D-mannitol, 1,4:3,6-dianhydro-2,5-dideoxy-2,5-dimethyl-D-glucitol, 1,4:3,6-dianhydrosorbitol-2,5-dimethyl-ether, or 1,4-phenylene, which is unsubstituted or substituted with an unbranched $C_1$-$C_6$-alkylen group, wherein one or more C-atom, —CH— or —$CH_2$-group, is not replaced, or, is replaced by —O—, —CO—, —COO—, —O(CO)—, or —O(CO)—O—, with the proviso that oxygen atoms are not directly linked to each other, and; and $R^1$, L, $r^1$ have the meaning and preferences as given above; and more preferred wherein $r^1$ is 0.

Especially more preferred is compound of formula (IV):

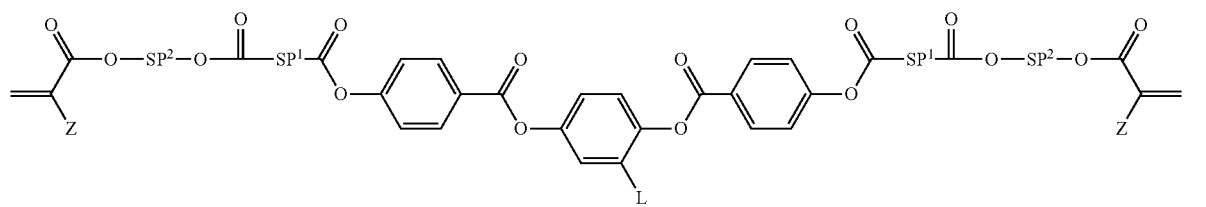

wherein $SP^1$, $SP^2$ and L have the same meanings and preferences as described above, and Z is hydrogen or methyl.

Further, more preferred are compounds (I) having an adhesion of >4, preferably of more than >5.

The adhesion values are based on the average of a 2 times testing, a removing test by pulling at 180° and then at 90° to the substrate, and belong to following scale:
5—0% of the area is removed
4—less than 10% of the area is removed
3—between 10-30% of the area is removed
2—between 30-50% of the area is removed
1—more than 50% of the area is removed
*removed area is the released area of the sample, which was stuck with an adhesive tape, which was then tried to pull at 180° and 90°.

The adhesion values are generated under the following standard procedure: First a surface area of a sample comprising compound (I) (manufactured in accordance to application/example 7 of this invention), which is free of defects such as for example scratch or dusts, and which is 1-2 cm away from the edges, is selected. Then an adhesive tape (Nichiban adhesive tape) is applied perpendicularly to the direction of the linearly polarised light used for orienting the orientation layer (at a temperature of 25° C. (+/−2° C.) and a humidity of 50% (+/−10%)) and strongly stuck on the lattice surface, and then let stayed there for 1 min waiting time. After this waiting time the adhesive tape is quickly removed by pulling first at 180° to the substrate and secondly at 90° to the substrate.

A further embodiment of the present invention relates to a liquid crystalline composition comprising at least a compound of formula (I) and optionally a further polymerisable liquid crystal compound and/or additive.

Polymerisable liquid crystal compounds are known in the art and especially preferred and herewith incorporated by reference are polymerisable liquid crystalline compounds described in WO 2005/105932, WO 2005/054406, WO 2004/085547, WO 2003/027056, US 2004/0164272, U.S. Pat. No. 6,746,729, U.S. Pat. No. 6,733,690, WO 2000/48985, WO 2000/07975, WO 2000/04110, WO, 2000/05189, WO 99/37735, U.S. Pat. No. 6,395,351, U.S. Pat. No. 5,700,393, U.S. Pat. No. 5,851,424 and U.S. Pat. No. 5,650,534.

More preferred is a liquid crystalline composition comprising at least a compound of formula (I), wherein $C^2$ is selected from the achiral groups $C^{2'}$ within the above-given meanings and preferences.

Further, more preferred is a liquid crystalline composition comprising compounds of formula (I), wherein $C^2$ is selected from the achiral groups $C^{2'}$ within the above-given meaning, and at least a single compound of formula (I), wherein $C^2$ is a chiral group selected from the groups $C^{2''}$ within the above-given meanings and preferences; or a composition comprising at least two different compounds of formula (I) with are $C^2$.

In addition, more preferred do liquid crystalline compositions comprise at least a compound (I), and at least a compound (III)

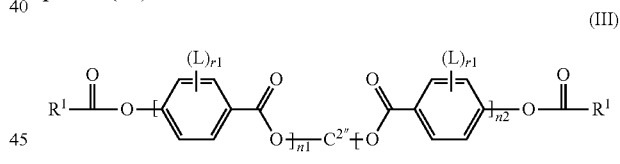

wherein $C^2$, $C^{2'}$ $R^1$, L, $r^1$, $n^1$, $n^2$ have the meanings and preferences as given above.

Further, more preferred do liquid crystalline compositions comprise at least a single compound (I), and three compounds (V), (VI) and (VII)

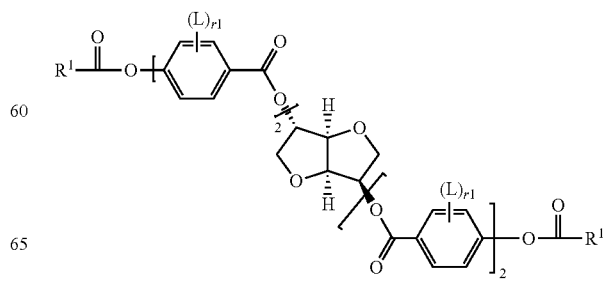

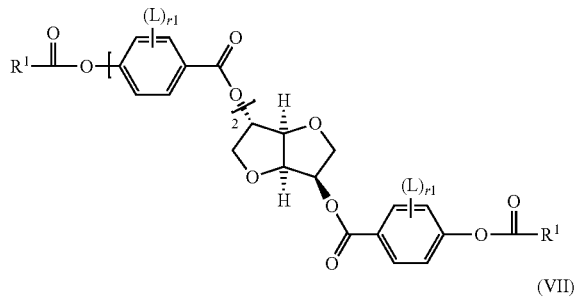

(VI)

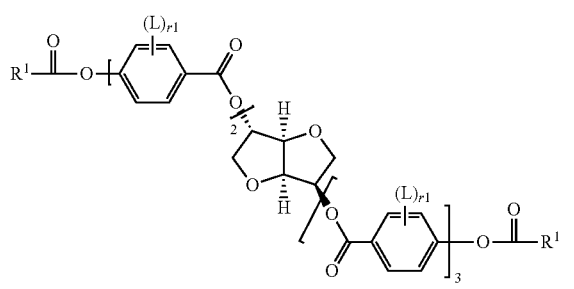

(VII)

wherein $R^1$, L and r1 have the above given meanings and preferences.

The amount of the components in a liquid crystalline composition depends on the envisaged use. If a liquid crystalline composition are desired the amount of components in the compositions of the invention is limited by the liquid crystal phase of the composition which has to be preserved. Conventionally, compound (I) with or without chiral groups $C^2$ have an amount of 0.1 to 99% by weight of the composition, preferably an amount of 1 to 50% by weight, even more preferably an amount of 1 to 30% by weight and especially even more preferably an amount of 1 to 10% by weight, with the proviso that the sum of the weight percentages of all components of the mixture is 100.

Further preferably the liquid crystalline compositions of the present invention comprise
a) 0.1 to 99.1% by weight of a compound (I), wherein $C^2$ is $C^{2\prime}$,
b) 0.1 to 99.1% by weight of a chiral compound (I), wherein $C^2$ is $C^{2\prime\prime}$,
wherein $C^2$, $C^{2\prime}$ and $C^{2\prime\prime}$ have the above-given meanings and preferences, and wherein the sum of the weight percentages of all components of the mixture is 100; preferably, the chiral component (I), is in an amount of 0.1 to 20% by weight in the composition.

In addition, preferably the liquid crystalline compositions of the present invention comprise compound (I) and reactive or not-reactive chiral compound.

Reactive and not-reactive chiral compounds are known in the art and described in U.S. Pat. No. 5,798,147 and herewith incorporated by reference.

Most preferred is a liquid crystalline composition comprising compounds of formula (I) and further components, such as for example additives, solvents.

Generally used additives are antioxidants, initiators, such as photoinitiators, accelerators, dyes, inhibitors, activators, fillers, chain transfer inhibitor, pigments, anti-static agents, flame-retardant agents, thickeners, thixotropic agents, surface-active agents, viscosity modifiers, extending oils, plasticizers, tackifiers, catalysts, sensitizers, stabilizers, such as e.g. phenol derivatives, such as 4-ethoxyphenol or 2,6-di-tert-butyl-4-methylphenol (BHT), lubricating agents; dispersing agents; a polymeric binder and/or monomeric compounds which can be converted into the polymeric binder by polymerization, or, in the case of emulsion coatings and printing inks, a dispersion auxiliary, such as disclosed in U.S. Pat. No. 5,798,147; hydrophobing agents, adhesive agents, flow improvers, defoaming agents, deaerators, diluents, auxiliaries, colorants, dyes and pigments, curing inhibitors, such as hydroquinone, p-tert.-butyl catechol; 2,6-di tert.-butyl-p-methylphenol; phenothiazine; N-phenyl-2-naphthylamine; or a photo-orientable monomer or oligomer or polymer as described in EP 1 090 325 B;

The amount of additives in the composition is limited by the requirement that the liquid crystal phase of the composition of the invention has to be preserved. Conventionally, the reactive or non reactive additives have an amount of 0.01 to 50% by weight of the composition, preferably an amount of 1 to 30% by weight, even more preferably an amount of 1 to 10% by weight.

In case the compositions of the invention comprise a stabilizer, the latter is generally present in an amount of 0.01 to 5% by weight of the composition, preferably in an amount of 0.1 to 1% by weight.

The initiator is employed in an amount effective for initiating cure of the composition. The effective amount depends upon the process parameters and starting material properties. Typical, the amount ranges from 0.01 to 10% by weight relative to the total weight % of the composition, preferably from 0.5 to 8% by weight, more preferred from 1 to 5% by weight. Combinations of two or more initiators (photo- or thermal initiators) may also be employed.

The liquid crystalline composition of the present invention is solid, or diluted in a solvent, which is an organic solvent and/or water, as a solution, gel, dispersion or emulsion.

Preferably, the composition is a clear solution. The solvent or solvent mixture used in the present application may be any compound that can dissolve the liquid crystal composition according to the invention. At least one solvent such as a common polar solvent or a nonpolar solvent may be used. The solvents which are particularly preferred are those leading to a good coatability or printability of the solution of the material to the substrate to be coated.

Most preferred does a liquid crystalline composition comprise compounds of formula (I) and a non-polar solvent.

Non-polar solvents are compounds that have low dielectric constants and are not miscible with water, such as preferably hexane, benzene, toluene, diethyl ether, 1,4-dioxane, tetrahydrofuran (THF), chloroform, ethyl acetate, dichloromethane, 1,3-dioxolane (DXG), and more preferably 1,3-dioxolane (DXG).

Polar solvent are aprotic or protic.

Most preferred does a liquid crystalline composition comprise compounds of formula (I) and a polar solvent.

Polar aprotic solvents are solvents that share ion dissolving power with protic solvents but lack an acidic hydrogen. These solvents generally have high dielectric constants and high polarity. Preferred polar solvents are acetone, acetonitrile (MeCN), dimethylformamide (DMF), dimethyl sulfoxide (DMSO), N-methylpyrrolidone (NMP), N-ethylpyrrolidone, N-vinylpyrrolidone, gamma.-butyrolactone (BL), N-methylmorpholine, propylene glycol diacetate, chlorobenzene, tetrahydrofuran, cyclopentanone (CP), methylethylketone (MEK), anisole (AN), cyclohexanone (CHN), methyl isobutyl ketone (MIBK), 1-methoxy-2-propanol acetate (MPA) and mixtures thereof.

Polar protic solvents are solvents, which contain dissociable H+, such as hydrogen fluoride. The molecules of such solvents can donate an H+ (proton). Conversely, aprotic solvents cannot donate hydrogen bonds. Common characteristics of protic solvents are to display hydrogen bonding, to have an acidic hydrogen (although they may be very weak acids), to be able to stabilize ions (cations by unshared free electron pairs, anions by hydrogen bonding). Examples are acetic acid, n-butanol, isopropanol, n-propanol, ethanol, methanol, formic acid, 2-butoxyethanol (BC), ethylcarbitol, butylcarbitol, ethylcarbitol acetate, ethylene glycol, propylene glycol monoacetate, dipropylene glycol, and dipropylene glycol monomethyl ether, and water.

Preferably the organic solvents used in the present application are protic or aprotic polar or non-polar solvents.

Preferred solvents are, however not limited to:
ketones such as for example acetone, cyclopentanone (CP), cyclohexanone (CH), methyl isobutyl ketone (MIBK), methylethylketone (MEK),
amides such as N,N-dimethylformamide (DMF), N-methylpyrrolidone (NMP), N-ethylpyrrolidone, N-vinylpyrrolidone, N,N-dimethylacetamide,
carbamates
ether such as tetrahydrofuran (THF), ethylene glycol, dipropylene glycol, butylcarbitol, ethylcarbitol acetate, dipropylene glycol monomethyl ether, 1,3-dioxolane (DXG)
ester such as ethyl acetate (EA), 1-methoxy-2-propanol acetate (MPA), gamma-butyrolactone (BL), propylene glycol monoacetate, propylene glycol diacetate,
alcohols, such as 2-butoxyethanol (BC), ethylcellosolve, butylcellosolve,
dimethyl sulfoxide (DMSO),
halogen hydrocarbons such as dichloromethane, chlorobenzene,
apolar solvents as for example, however not limited to hydrocarbons, such as hexane, heptane, toluene; anisol, petrolether.
and mixtures thereof.

More preferred solvents are acetone, cyclopentanone (CP), cyclohexanone (CH), methyl isobutyl ketone (MIBK), methylethylketone (MEK), N,N-dimethylformamide (DMF), N-methylpyrrolidone (NMP), N-ethylpyrrolidone, N-vinylpyrrolidone, N,N-dimethylacetamide, (AN), tetrahydrofuran (THF), 1,3-dioxolane (DXG), ethylene glycol, dipropylene glycol, butylcarbitol, ethylcarbitol acetate, dipropylene glycol monomethyl ether, ethyl acetate (EA), 1-methoxy-2-propanol acetate (MPA), gamma-butyrolactone (BL), propylene glycol monoacetate, propylene glycol diacetate, dipropylene glycol monomethyl ether, dimethyl sulfoxide (DMSO).

Most preferred are cyclopentanone (CP), cyclohexanone (CH), methyl isobutyl ketone (MIBK), methylethylketone (MEK), ethyl acetate (EA), 1-methoxy-2-propanol acetate (MPA), 1,3-dioxolane (DXG), dimethyl sulfoxide (DMSO).

Depending on the envisaged use, it can be of advantage to add a solvent. Typical concentrations of the compositions disposed in a solvent are between 2 and 50%, preferred between 10 and 40% by weight of the active ingredients, such as compound (I) and optionally an additive, in said solvent.

The compounds (I) of the present invention can be prepared by method known in the art.

Further, the present invention relates also to a process for the preparation of ester group comprising compounds, preferably compound (I),
comprising
a) bringing into contact a compound of formula (VIII)

$$P\text{-}Sp^2\text{---}OH \quad (VII)$$

with a compound of formula (IX)

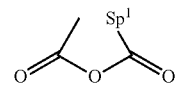

(IX)

b) and a dihydroxy compound of formula (XI)

$$HO\text{---}(C^1\text{---}X^1)n^1\text{---}C^2\text{---}(X^2\text{---}C^3)n^2\text{---}OH \quad (XI);$$

or a compound of formula (XII)

$$HO\text{---}(C^1\text{---}X^1)n^1\text{---}C^2\text{---}(X^2\text{---}C^3)n^2\text{---}Y \quad (XII)$$

wherein P, $Sp^2$, $Sp^1$, $C^1$, $C^2$, $C^3$, $n^1$, $n^2$ have the same meanings as described above, Z is hydrogen or methyl and Y represents COOH, $COOC_1\text{---}C_6$alkyl, halogen or CN, Y is preferably CN.

Preferably, the steps a) and b) are conducted in a "one pot reaction", or alternatively the process can be conducted in more than one step, by isolating for example the intermediate generated in step a).

Preferably the compounds are brought in contact by coupling them.

In general, the coupling in steps a) can be conducted with or without solvent. However, it may be of advantage to use solvents, such as polar or unpolar aprotic solvents within the below given meaning of solvents. Preferred solvents are tetrahydrofuran, toluene, xylene.

Process step b) is preferably conducted in the presence of a solvent, preferably of an aprotic solvent.

Further, the coupling steps a) and b) can be conducted in the presence of stabilizers, 2,6-di-tert-butyl-4-methyl-phenol.

Preferably, steps a) is conducted in the presence of a base such as a tertiary amine.

The temperature of the coupling steps a) and b) depends on the reacting parameters such as the reacting material used.

Preferably, step a) is conducted by elevated temperature up to for example 30 to 180° C.

Preferably, the molar ratio of the starting materials in step a) is for example in the range of 1:0.8 to 0.8:1 and depends on the reactivity and solubility of the used solvents.

Preferably, the molar ratio of the dihydroxy (XI) to the compound obtained in step a) is for example in the range of (0.5:1 to 0.1:1); and the molar ratio of the monohydroxy compound of formula (XII) to the compound obtained in step a) is for example in the range of (1:1 to 1:0.8).

The coupling of step b) is preferably conducted by esterification of the activated carboxylic acids, such as acid chlorides, or by carbodiimide coupling, or by using a mixed anhydride such as methansulfonylchloride, of the compound obtained in step a). Preferably, step b) is conducted in the presence of DMAP or pyridine.

The acid chloride of compound obtained in step a) can be conducted according to known processes for the formation of acid chlorides, such as described in standard books. Also the carbodiimide coupling and the reaction with mixed anhydrides can be conducted under known processes described in standard books of chemistry.

The hydroxyalkyl acrylates are either commercial products or can be easily prepared by reaction of e.g. acrylic chloride with dihydroxy compound.

The compounds $HO\text{---}(C^1\text{---}X^1)n^1\text{---}C^2\text{---}(X^2\text{---}C^3)n^2\text{---}OH$ (XI) or $HO\text{---}(C^1\text{---}X^1)n^1\text{---}C^2\text{---}(X^2\text{---}C^3)n^2\text{---}Y$ (XII)

are known and can be synthesized according to literature methods (e.g. JP 11080090). They can for example be prepared by or in analogy to the reaction of 4-hydroxybenzoic acid with toluhydroquinone in para-toluenesulfonic acid monohydrate in an aprotic solvent such as o-xylene.

A further embodiment of the present invention relates also to a process for the preparation of compound (I) comprising
a) coupling a dihydroxy compound (XI), HO—($C^1$—$X^1$)$n^1$—$C^2$—($X^2$—$C^3$)$n^2$—OH (XI) or a monohydroxy compound of formula (XII), HO—($C^1$—$X^1$)$n^1$—$C^2$—($X^2$—$C^3$)$n^2$—Y (XII) with a compound of formula (IX)

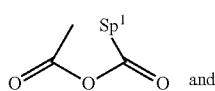

(IX)

and b) then, coupling the compound obtained in step a) with

P-$Sp^2$—OH  (VIII)

wherein P, $SP^2$, $SP^1$, $C^1$, $C^2$, $C^3$, $n^1$, $n^2$ Y have the above-given meanings and preferences.

The reaction conditions of steps a) and b) and preferences are as described above for the process of the preparation of compound (I), with the proviso that the starting material is replaced and the molecule ratios are adapted accordingly.

In addition, the present invention relates to the product obtained by a process described above.

Further, the present invention comprises methods for the preparation of an unpatterned or patterned birefringent layer comprising polymerising compound (I) or the composition according to the invention.

The present invention also comprises the use of the compound (I) or the composition of the invention for the preparation of an unpatterned or patterned birefringence layer.

Preferably, the term "patterning" denotes to birefringence patterning and/or thickness patterning and/or patterning of the optical axis orientation, and/or patterning of the degree of polymerization, and preferably comprising photo-polymerizing. Birefringence denotes the difference between the extraordinary and the ordinary index of refraction.

The term "unpatterned" denotes to an uniform oriented birefringence layer over the whole area of the layer.

Further, the present invention comprises a method for the preparation of a birefringence layer comprising polymerizing preferably on an aligning surface a compound (I) or the composition of the invention.

In the context of the present invention aligning surface shall mean any surface of a substrate that has aligning capabilities for liquid crystals.

The substrate is for example plastic such as PET, polyethylenterephthalate, or TAC, cellulose triacetate, or any other material such as glass that can be optionally coated with indium tin oxide (ITO). Further, the substrates may comprise coatings which generate or transfer such aligning capabilities. Such coatings are well known as alignment layers.

Alignment layers can be prepared using any technique known in the art, which include but is not limited to rubbing, such as rubbed polyimide or polyamic acid, embossing, scratching, oblique deposition of SiO or the like, photolithographic grating, LB films (Langmuir Bodgett films), SAMS (Self Assembled Monolayer Surface), ion irradiation process, laser writing of surface structures, alignment texture transfer by stamping, photo-alignment including for example photo-polymerization, photo-dimerization, photo-decomposition, photo-isomerisation.

Preferred alignment layer is a layer of photo-oriented photo-topopolymers. For the preparation of alignment layers the composition of the invention is applied on a substrate and photo-polymerized. Photo-polymerization means that the composition is cured using light, preferably UV light and more preferably UVA, to give a cross-linked birefringent layer. The curing time is dependent, inter alia, on the reactivity of the polymerizable material, the thickness of the coated layer, the type of the polymerization initiator and the power of the UV lamp. Preferred are linearly photo-polymerized alignment layers. Preferred aligning surfaces are PET and alignment layers, especially photo alignment layers.

The present invention also relates to a process for the preparation of a birefringent layer comprising compound (I) or a composition according to the invention.

Preferably the process for the preparation of a birefringent layer comprises
a) coating or printing compound (I) or a composition of the invention on an aligning surface,
b) optionally drying, and
c) then, polymerizing, preferably photopolymerizing.

In general the composition is applied by general coating and printing methods known in the art. Coating methods are for example spin coating, air doctor coating, blade coating, knife coating, reverse-roll coating, transfer roll coating, gravure roll coating, kiss roll coating, cast coating, spray coating, slot-orifice coating, calendar coating, electrodepositing coating, dip coating or die coating.

Printing methods are for example relief printing such as flexographic printing, ink jet printing, intaglio printing such as direct gravure printing or offset gravure printing, lithographic printing such as offset printing, or stencil printing such as screen printing.

It depends on the consistence of the composition whether a drying step is conducted. If solvents are comprised by the composition, the composition is usually dried after the applying step.

In general "drying" consists in the extraction of the solvent(s) for example by application of heated gas using for example an air stream that applies the heat by convection and carries away the vapor of solvents (convective or direct drying). Drying is faster at higher temperatures. In addition, product or film qualities also have to be considered in the determination of the temperature applied for the drying. Other possibilities are vacuum drying, where heat is supplied by contact conduction or radiation (or microwaves) while the produced vapor is removed by the vacuum system; indirect or contact drying (heating through a hot wall), as drum drying, vacuum drying; dielectric drying (radiofrequency or microwaves being absorbed inside the material); freeze drying or lyophilization; mechanical extraction of the solvent.

In a preferred embodiment of the invention, the process comprises photo-polymerizing the applied compound (I) or the composition obtained in step a) or b). The photo-polymerizing is conducted by radiation.

In the context of the present invention radiation is polarized or unpolarized light.

Preferred is unpolarized light, but in specific cases polarized or partially polarized, linearly, circularly or elliptically polarized light can also be applied.

Conventionally, a lamp is used for photo-polymerization. The intensity of the lamp used for the irradiation should be preferably higher than 0.2 mW/cm$^2$, more preferably higher than 10 mW/cm$^2$, most preferably higher than 20 mW/cm$^2$, especially most preferably higher than 50 mW/cm$^2$.

The photo-polymerizing is also accessible by electron beam (EB).

The present invention also relates to the use of the unpatterned or patterned birefringence layer for optical or electro-optical components and systems, especially multilayer systems, or devices.

Further, the present invention also relates to a method for the preparation of optical or electro-optical components and systems, especially multilayer systems, or devices, which may comprise cholesteric layers, and/or unpatterned or patterned birefringence layer of the present invention.

Patterned or patterned birefringent layer comprising polymerised compound (I) or the composition of the invention.

An optical component, system or device creates, manipulates, or measures electromagnetic radiation.

An electro-optical component, system or device operates by modification of the optical properties of a material by an electric field. Thus it concerns the interaction between the electromagnetic (optical) and the electrical (electronic) states of materials.

The present invention further relates to an optical or electro-optical component comprising compound (I) or the composition of the invention.

Preferably, the unpatterned or patterned optical or electro-optical component, can be used for (but are not limited to) a waveguide, a security or brand protection element, a bar code, an optical grating, a filter, a retarder, a compensation film, a reflectively polarizing film, an absorptive polarizing film, an anisotropically scattering film compensator and retardation film, a twisted retarder film, a cholesteric liquid crystal film, a guest-host liquid crystal film, a monomer corrugated film, a polarizer, a piezoelectric cell, a thin film exhibiting non-linear optical properties, a decorative optical element, a brightness enhancement film, a component for wavelength-band-selective compensation, a component for multi-domain compensation, a component of multiview liquid crystal displays, an achromatic retarder, a polarization state correction/adjustment film, a component of optical or electro-optical sensors, a component of brightness enhancement film, a component for light-based telecommunication devices, a patterned G/H-polarizer with an anisotropic absorber, a patterned reflective circular polarizer, a patterned reflective linear polarizer, a patterned MC (monomer corrugated film).

Preferred are security elements, especially transmissive or reflective one; polarizer, compensator and retardation films.

A further aspect of the invention provides an optical or electro-optical component and multi-layer system comprising a compound (I) or composition according to the invention.

In addition, the present invention relates to a method for the preparation of optical or electro-optical component comprising compound (I) or the composition of the invention.

Preferably, the present invention relates also to the use of unpatterned or patterned optical or electro-optical component according to the invention
as retardation film and/or compensation film and/or reflectively polarizing film and/or absorptively polarizing film and/or anisotropically scattering film for
(a) twisted nematic (TN) liquid crystal displays, hybrid aligned nematic (HAN) liquid crystal displays, electrically controlled birefringence (ECB) liquid crystal displays, supertwisted nematic (STN) liquid crystal displays, optically compensated birefringence (OCB) liquid crystal displays, pi-cell liquid crystal displays, in-plane switching (IPS) liquid crystal displays, fringe field switching (FFS) liquid crystal displays, vertically aligned (VA) liquid crystal displays; all above display types are applied in either transmissive or reflective or transflective mode;
(b) displays generating three dimensional images or images varying with viewing angle;
(c) security or brand protection devices;
(d) decorative optical devices;
(e) brightness enhancement films;
(f) optical sensors;
(e) light-based telecommunication devices.

Further, preferably the present invention relates to a monomer corrugated film.

Further, preferably the present invention relates to stacks of above given devices.

A further embodiment of the present invention relates to devices comprising an optical or electro-optical component, preferably compensation and retardation films (viewing angle, color shift, contrast, gray level stability, brightness) for:
security elements, such as transmissive and reflective ones;
wavelength-band-selective compensation: birefringent compensation film which is patterned according to the RGB, red, green and blue, subpixels of the liquid crystal display to provide compensation properties optimally adapted to the respective wavelength band transmitted by the subpixel,
multi-domain (e.g. transflective liquid crystal displays) compensation: birefringent compensation film with patterned properties according to the laterally varying properties of the device to be compensated,
component of multiview liquid crystal displays: compensation or retardation film as a component of a display providing different images for different viewing angles,
component of three dimension liquid crystal displays: compensation or retardation film used as a component of a liquid crystal display providing three dimensional image information,
achromatic retarder: retarder film which in contrast to a simple chromatic retarder provides for a similar change in polarization state for a broader wavelength band, e.g. the whole visible wavelength spectrum,
polarization state correction/adjustment films: birefringent films which are used to correct or adjust the polarization state with the goal to enable the function or improve the performance of an optical device,
component of optical or electro-optical sensors, in particular polarization sensitive/selective sensors,
component of brightness enhancement film,
security devices or decorative optical devices,
components for light-based telecommunication devices, in particular devices based on polarized light.

A further embodiment of the present invention relates to devices comprising a patterned G/H-polarizer with an anisotropic absorber.

Preferably the patterned G/H-polarizer with an anisotropic absorber is a thin film polarizer, in-cell polarizer, a security device or a decorative optical device.

A further embodiment of the present invention relates to devices comprising a patterned reflective circular polarizer.

Preferably the patterned reflective circular polarizer is a brightness enhancement film, a security device or a decorative optical device.

A further embodiment of the present invention relates to devices comprising a patterned reflective linear polarizer.

Preferably the patterned reflective linear polarizer is a brightness enhancement film, a security device or a decorative optical device.

A further embodiment of the present invention relates to a beam steering device, which comprises an optical or electro-optical component, preferably compensation and retardation films for wavefront adjustment devices.

A further embodiment of the present invention relates to devices comprising a patterned MC, monomer corrugated, film.

Preferably the patterned monomer corrugated film is an anisotropically scattering film, an anisotropic reflector, an anti-reflection film, a film with enhanced birefringence, a security device or a decorative optical device.

Especially preferred are in the present invention devices such as for example twisted nematic (TN) liquid crystal displays, hybrid aligned nematic (HAN) liquid crystal displays, electrically controlled birefringence (ECB) liquid crystal displays, supertwisted nematic (STN) liquid crystal displays, optically compensated birefringence (OCB) liquid crystal displays, pi-cell liquid crystal displays, in-plane switching (IPS) liquid crystal displays, fringe field switching (FFS) liquid crystal displays, vertically aligned (VA) liquid crystal displays; all above display types are applied in either transmissive or reflective or transflective mode, which can be used for displays generating three dimensional images or images varying with viewing angle; beam steering device; a light-based telecommunication device; optical sensor; stacks of devices.

In the present invention novel compounds (I) and compositions were found, which exhibit a broad liquid-crystalline thermal range, which have good adhesive properties to substrates and aligning surfaces. Further, these compounds are accessible by way of a simple process. This easy accessibility is very useful for various applications.

EXAMPLES

Definitions Used in the Examples

TAC=Triacetylcellulose
LPP has the meaning of "linearly photo-orientable polymer".
  For the production of an alignment layer, suitable LPP materials are described for example in patent publications EP 0 611 786, WO 96/10049 and EP 0 763 552, and include cinnamic acid derivatives and ferulic acid derivatives. For the following examples, the LPP material as described in U.S. Pat. No. 6,107,427, example 4, is chosen.
  This photo-alignment polymer is based on cinnamate as photo-reactive groups. The polymer backbone of the photo-alignment material is of acrylate type.
CHN=cyclohexanon
CP=cyclopentanon
AD42=Irgacure 369, 2-benzyl-2-dimethylaminio-1-(4-morpholinophenyl)-butanone-1 commercially available from BASF
AD282: Irgacure 907, 2-methyl-1[4-(methylthio)phenyl]-2-morpholino-propan-1-one
AD138: Tris (2,4-di-tert-butylphenyl)phosphate commercially available from Aldrich
AD184: Tego Flow 300, solution of polyacrylates, from EVONIK
AD43=BHT, 2,6-di-tert-butyl-4-methyl-phenol, commercially available from Fluka
PP=Polypropylen
K=crystal form
N=nematic phase
I=isotropic phase
M=liquid crystalline phase
$(S_A)$=monotrop smectic A phase Preparation Example 1

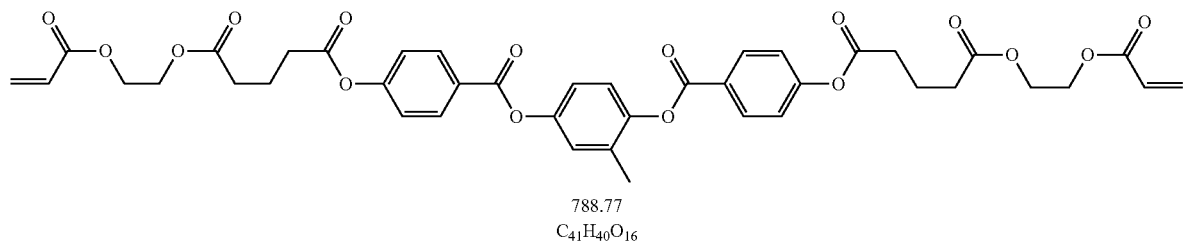

(XIII)

788.77
$C_{41}H_{40}O_{16}$ 1.1) Preparation (XIII) by Variant a)

1.1.1) A mixture consisting of 276.24 g 4-hydroxybenzoic acid, 124.12 g toluhydroquinone, 20.00 g p-toluenesulfonic acid monohydrate and 1800 ml o-xylene in a chemical reactor equipped with stirrer, thermometer and separator for the azeotropic removal of water under reflux is heated to reflux in an oil bath of 178° C. Refluxing and separation of water starts at a vapour temperature of ca. 137° C. and is continued for a total of 18 hours with ca. 35 ml of water separated. A beige, slightly viscous suspension is formed. It is cooled to 65° C. and 1250 ml of toluene are added. After further cooling to 25° C. the mixture is stirred for 30 minutes at this temperature and then filtered. The crystalline filter residue is washed with toluene to yield a beige solid. The orange filtrates are discarded. The solid is suspended in 1250 ml ethyl acetate and stirred for 1 hour at 45° C. The suspension is cooled to 6° C., filtered, the filter residue washed with ca. 800 ml of ice-cold ethyl acetate and dried in vacuum at 50° C. to constant weight to yield 341.60 g nearly colourless diphenol (XIV). HPLC purity is 99 area %

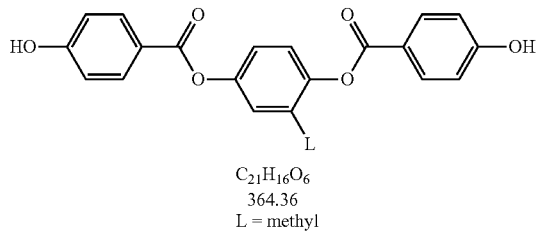

(XIV)

$C_{21}H_{16}O_6$
364.36
L = methyl 1.1.2) A mixture of 156.76 g 2-hydroxyethyl acrylate, 154.04 g glutaric anhydride and 0.40 g 2,6-di-tert.-butyl-4-methyl-phenol is loaded into a chemical reactor equipped with stirrer and thermometer. The mixture is heated to ca. 30° C. and stirred until a homogeneous solution is attained. The heating is stopped and 4.725 ml of triethylamine are added. The exothermic reaction drives the temperature to ca. 90° C. within 15 minutes. Cooling is applied to keep the temperature below 90° C. After the exotherm has subsided the reaction mixture is kept at 75° C. for 2.5 hours and cooled to ambient temperature. The acid (XV) is obtained as a colourless, viscous liquid in quantitative yield.

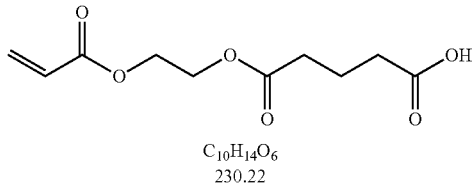

(XV)

$C_{10}H_{14}O_6$
230.22

1.1.3.) The mixture consisting of 218.60 g of the diphenol (XIV), 322.20 g of the acid (XV), 24.40 g 4.dimethylaminopyridine, 2.50 g 2,6-di-tert.butyl-p-cresol (BHT) and 1400 ml toluene in a chemical reactor equipped with stirrer, thermometer and addition funnel is cooled to +4° C. The solution of 289.00 g dicyclohexylcarbodiimid (DCC) in 500 ml toluene is added within 1 hour, keeping the reaction temperature below +10° C. The cooling device is removed and the reaction mixture stirred overnight (16 hours) at room temperature (22-25° C.). To the suspension are added 1000 ml of a aqueous 5%-solution of sodium bicarbonate, stirring continued for 15 minutes, and then the mixture is filtered to remove the precipitated DCC-urea. The 2-phase filtrate is separated and the lower aqueous phase discarded. The toluene phase is once washed with 1000 ml 10%-sodium chloride solution and the toluene partly distilled off to yield ca. 825 g of a yellow solution. It is diluted with 825 ml toluene to give a solid content of ca. 35%. The product is crystallized by slowly adding this solution to 4720 ml of isopropanol, cooled to –10° C. The suspension is stirred for 1 hour at –10° C., filtered and the crystalline product dried in vacuum at 25° C. to constant weight. The yield of colourless, crystalline product (XIII) is 470 g.

Analytical Data:
HPLC purity: 93 area %
Melting point: 5° C.

1.2) Preparation (XIII) by Variant b)

1.2.1 A mixture of 17.4 g 2-hydroxyethyl acrylate, 17.1 g glutaric anhydride and 0.05 g 2,6-di-tert.-butyl-4-methyl-phenol is loaded into a chemical reactor equipped with stirrer and thermometer. THF 60 mL and 22 g of triethylamine are added to the mixture. The solution is heated to 50° C. and stirred for two hours. The solution is cooled to –30° C. and a mixture of 23 g of triethylamine and 18.9 g of methansulfonyl chloride is added in drops. After 1.5 h, 10.9 g of diphenol (XIV) and 1.5 g of 4-dimethylaminopyridine in 60 mL tetrahydrofuran are added to the mixture and stirred overnight (16 hours) at room temperature (22-25° C.). The mixture is filtrated off through celite and silica gel. The solution is extracted with 200 mL of ethyl acetate, washed with 100 mL of HCl 0.5N and 100 mL of water. The organic phase is dried over sodium sulfate, and the excess of solvent is removed under vacuum. Purification on chromatography column: SiO2, cyclohexyl/ethyl acetate 6/4 as eluent, gives a 19 g of a slight yellow oil. The product is crystallized by slowly adding 30 mL ethanol to a solution made by 19 g of product solubilised in 20 mL ethyl acetate cooled at –10° C. The suspension is stirred for 1 hour at –10° C., filtered and the crystalline product is dried in vacuum at 25° C. to constant weight. The yield of colourless, crystalline product (XIII) is 13.3 g. Analytical data:

HPLC purity: 96 area %
Melting point: 5° C.
Mass spectroscopy +EMS: 806.4 M $NH_4^+$ According to the synthesis of Example 1/Variant b) the below in Table 1 listed compounds are prepared, with the proviso that for the preparation of B1, 2-hydroxyethyl acrylate, is replaced by 2-hydroxyethyl methacrylate and glutaric anhydride is replaced by maleic anhydride;

of B2, glutaric anhydride is replaced by maleic anhydride;

of B3, 2-hydroxyethyl acrylate, is replaced by 2-hydroxyethyl methacrylate and glutaric anhydride is replaced by maleic anhydride and the reactant methansulfonyl chloride is replaced by thionyle chloride;

of B4, 2-hydroxyethyl acrylate, is replaced by 2-hydroxypropyl acrylate;

of B5, 2-hydroxyethyl acrylate, is replaced by 2-hydroxybutyl acrylate;

of B6, 2-hydroxyethyl acrylate, is replaced by 4-hydroxybut-2-enyl-acrylate;

of B7, 2-hydroxyethyl acrylate, is replaced by 2-hydroxypentyl acrylate;

TABLE 1

| Structure $R^1$ | Liquid crystalline properties | Mass spectroscopy +EMS |
|---|---|---|
| B1 | K-78-N-158-I Supercooling 20° C. | 802.2 M $NH_4^+$ |

TABLE 1-continued
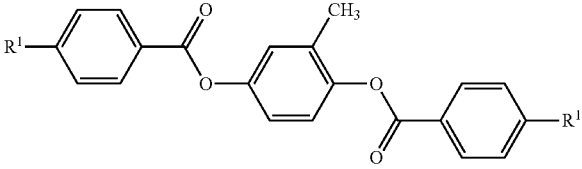
| Structure R$^1$ | Liquid crystalline properties | Mass spectroscopy +EMS |
|---|---|---|
| 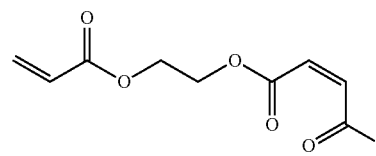<br>B2 | K-78-N-192-I<br>Supercooling 20° C. | 774.2 M NH$_4^+$ |
| 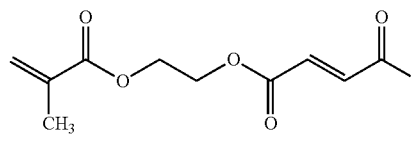<br>B3 | K-82-N-161-I<br>Supercooling to 52° C. | 802.2 M NH$_4^+$ |
| 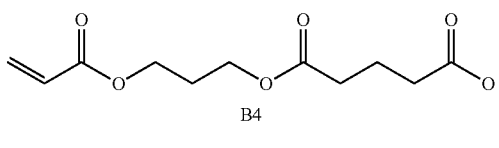<br>B4 | K-54-N-83-I<br>Supercooling to 39° C. | 834.3 M NH$_4^+$ |
| 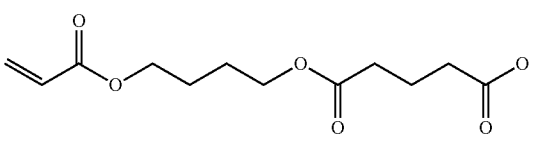<br>B5 | K-60-N-75-I<br>Supercooling to 35° C. | 862.5 M NH$_4^+$ |
| 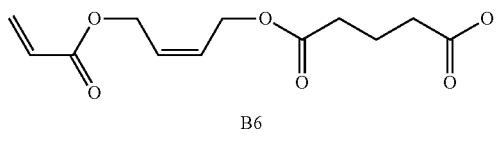<br>B6 | K-52-N-79.5-I<br>Supercooling to 20° C. | 858.3 M NH$_4^+$ |
| 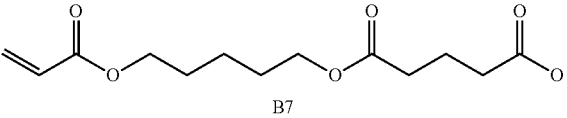<br>B7 | K-34-N-70.5-I<br>Supercooling 20° C. | 890.3 M NH$_4^+$ |

According to the synthesis of Example 1/Variant b) the below in Table 2 listed compounds are prepared, with the proviso that for the preparation

- of C1, diphenol (XIV), which is prepared according to example 1.1.1) is replaced by a diphenol, wherein L is hydrogen, and the starting material toluhydroquinone is replaced by hydroquinone;
- of C2, diphenol (XIV), which is prepared according to example 1.1.1) is replaced by a diphenol, wherein L is methoxy, and the starting material toluhydroquinone is replaced by 2-methoxy-hydroquinone;

TABLE 2

| L = | Liquid crystalline properties | Mass spectroscopy +EMS |
|---|---|---|
| H (C1) | K-114-M | 792.3 M $NH_4^+$ |
| O-methyl (C2) | K-45-(N)-Iso monotrope | 822.2 M $NH_4^+$ |

Example 2

Synthesis of a Mono Reactive Compound

According to the synthesis of Example 1/Variant b) the below, in table 3, listed compounds are prepared, with the proviso that for the preparation of D3, diphenol (XIV) is replaced by

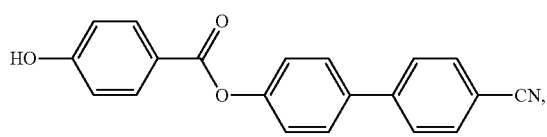

which is prepared in analogy to example 1.1.1) from 4-hydroxybenzoic acid and 4-hydroxy-4'-cyano-biphenyl-.

TABLE 3

|  | Mass |
|---|---|
| D3 | 545.3 M $NH_4^+$ |

Liquid crystallinity
K-105-($S_A$)-153N-159-I

Application/Example 1a

Retarder/Quarter Wave Plate (on TAC Substrate with Hard Coat)

A 40 micron thick hard coated TAC foil is corona treated (parameters: Power=0.3 kW; rotation speed 120 m/min; No of turns: 6) and then K bar (size 0) coated with a LPP solution (2% solid content in 80% MEK and 20% CHN). The wet film is dried at 80° C. for 60 s; the dry film thickness was about 60 nm. Then the dry film is exposed to linearly polarized collimated UVB light (25 mJ/cm$^2$)

Then the sample is k bar (size 1) coated with a 30% formulation of 98.4% compound (XIII) as synthesized in example 1
1.0% AD42
0.5% AD184
0.1% AD43 in a solvent mixture of 80% MEK and 20% CHN. The wet film is annealed and dried at 60° C. for 120 s and cross-linked under nitrogen with 1 J/cm$^2$ of un-polarized UVA light. After this treatment the film exhibited an uni-axial, uniform (=unpatterned, equal birefringent of the whole area of the film) anisotropy without visible defects. The thickness of the cross linked polymer film turns out to be 1310 nm. The film exhibits an optical retardance of 135 nm at 550 nm.

Application/Example 1b

Retarder/Quarter Wave Plate (on TAC Substrate with Hard Coat)

A 40 micron thick hard coated TAC foil was corona treated (parameters: Power=0.3 kW; rotation speed 120 m/min; No of turns: 6) and then K bar (size 0) coated with a LPP solution (2% solid content in 80% MEK and 20% CHN). The wet film was dried at 80° C. for 60 s; the dry film thickness was about 60 nm. Then the dry film was exposed to linearly polarized collimated UVB light (25 mJ/cm$^2$)

Then the sample was k bar (size 1) coated with a 30% formulation of 95.4% compound (XIII) as synthesized in example 1
4.0% AD282
0.5% AD184
0.1% AD43 in a solvent mixture of 80% DXG and 20% CHN. The wet film was annealed and dried at 60° C. for 120 s and cross-linked under air atmosphere with 1.5 J/cm$^2$ of un-polarized UVA light. After this treatment the film exhibited an uni-axial, uniform (=unpatterned, equal birefringent of the whole area of the film) anisotropy without visible defects. The thickness of the cross linked LCP film turned out to be 1310 nm. The film exhibited an optical retardance of 135 nm at 550 nm.

Application/Example 2

Half Wave Plate (on TAC Substrate with Hard Coat)

A 40 micron thick hard coated TAC foil is corona treated (parameters: Power=0.3 kW; rotation speed 120 m/min; No of turns: 6) and then K bar (size 0) coated with a LPP solution (2% solid content in 80% MEK and 20% CHN). The wet film is dried at 80° C. for 60 s; the dry film thickness was about 60 nm. Then the dry film is exposed to linearly polarized collimated UVB light (25 mJ/cm$^2$).

Then the sample is k bar (size 2) coated with a 40% solution of
    98.4% compound (XIII) as synthesized in example 1
        1.0% AD42
        0.5% AD184
        0.1% AD43
in a solvent mixture of 80% MEK and 20% CHN. The wet film is annealed and dried at 60° C. for 120 s and cross-linked under nitrogen with 1 J/cm$^2$ of un-polarized UVA light. After this treatment the film exhibited an uni-axial, uniform anisotropy without visible defects. The thickness of the cross linked polymer film turned out to be 2620 nm. The film exhibited a retardance of 270 nm at 550 nm. It is well suited for half wave plate applications. Other intermediate retarder plates are also feasible.

Application/Example 3

Security Element (Reflective)

A 20 micron thick metalized PP foil is corona treated (parameters: Power=0.3 kW; rotation speed 120 m/min; No of turns: 6) and then K bar (size 0) coated with a LPP solution (2% solid content in a solution of 80% MEK and 20% CHN). The wet film is dried at 80° C. for 120 s; the dry film thickness was about 60 nm. Then the dry film is first exposed to linearly polarized collimated UVB light (25 mJ/cm$^2$; polarization azimuth angle $\phi$=0° through a mask and subsequently with 10 mJ/cm$^2$ without mask at a polarization azimuth angle of $\phi$=45°.

Then the sample is k bar (size 1) coated with a 30% solution of
    98.4% (XIII) as synthesized in example 1
        1.0% AD42
        0.5% AD184
        0.1% AD43
in a solvent mixture of 80% MEK and 20% CHN. The wet film is annealed and dried at 60° C. for 120 s and cross-linked under nitrogen with 1 J/cm$^2$ of un-polarized UVA light. After this treatment the film exhibited a patterned uni-axial anisotropy without visible defects. The thickness of the cross linked polymer film turns out to be 1310 nm and exhibited a retardance of 135 nm at 550 nm. The optical axis of the birefringent film is oriented 0° in the areas which were covered by the mask in a first exposure and is uniformly oriented along the 45° polarization azimuth angle in areas which were subsequently exposed without a mask.

When the sample is observed using a polarizer then the pattern is easily visible showing either a positive or a negative image depending on the orientation of the polarizer. This feature can be used for second level security elements.

Application/Example 4

Security Element (Transmissive)

A 40 micron thick hard coated TAC foil is corona treated (parameters: Power=0.3 kW; rotation speed 120 m/min; No of turns: 6) and then K bar (size 0) coated with a LPP solution (2% solid content in a solution of 80% MEK and 20% CHN). The wet film is dried at 80° C. for 120 s; the dry film thickness is about 60 nm. Then the dry film is first exposed to linearly polarized collimated UVB light (25 mJ/cm$^2$; polarization azimuth angle $\phi$=0° through a mask and subsequently with 10 mJ/cm$^2$ without mask at a polarization azimuth angle of $\phi$=45°

Then the sample is k bar (size 1) coated with a 40% solution of
    98.4% compound (XIII) as synthesized in example 1
        1.0% AD42
        0.5% AD184
        0.1% AD43
in a solvent mixture of 80% MEK and 20% CHN. The wet film is annealed and dried at 60° C. for 120 s and cross-linked under nitrogen with 1 J/cm$^2$ of un-polarized UVA light. After this treatment the film exhibits a patterned uni-axial anisotropy without visible defects. The thickness of the cross linked birefringent film turns out to be 2610 nm. The film exhibits a retardance of 270 nm at 550 nm. The optical axis of the birefringent film is oriented 0° in the areas which are covered by the mask in a first exposure and is uniformly oriented along the 45° polarization azimuth angle in areas which are subsequently exposed without a mask.

When the sample is observed between crossed polarizers (in transmission) then the pattern is easily visible showing either a positive or a negative image depending on the orientation of the sample.

Application/Example 5

Cholesteric Circular Reflection Layer

A 40 micron thick hard coated TAC foil is corona treated (parameters: Power=0.3 kW; rotation speed 120 m/min; No of turns: 6) and then K bar (size 0) coated with a LPP solution (2% solid content in a solution of 80% MEK and 20% CP). The wet film is dried at 80° C. for 120 s; the dry film thickness was about 60 nm. Then the dry film is exposed to linearly polarized collimated UVB light (25 mJ/cm$^2$)

Then the sample is k bar (size 0) coated with a 2% formulation of
    98.4% compound (XIII) as synthesized in example 1
        1.0% AD42
        0.5% AD184
        0.1% AD43
in a solvent mixture of 80% MEK and 20% CHN. The wet film is annealed and dried at 60° C. for 120 s and cross-linked under nitrogen with 1 J/cm$^2$ of un-polarized UVA light. After this treatment the film exhibits an uni-axial uniform anisotropy without visible defects. The thickness of the cross linked polymer film turns out to be about 50 nm.

Then the sample is k bar (size 2) coated with a 40% solution of
    94.4% compound (XIII) as synthesized in example 1
        4.0% Lumogen S750 (commercially available by BASF)
        1.0% AD42
        0.5% AD138
        0.1% AD43 in MPK. The wet film is annealed and dried at 50° C. for 120 s and cross-linked under nitrogen with 1 J/cm² of un-polarized UVA light. After this treatment the film exhibits a cholesteric orientation with a reflection band centred at 620 nm and the width of the selective reflection band of is about 40 nm. The layer appeared uniform without visible defects. The thickness of the cross linked cholesteric film turned out to be 2500 nm. It is well suited for circular reflection filter applications in the region of the selective reflection.

Application/Example 6a

Cholesteric Circular Polarizer

A 40 micron thick hard coated TAC foil was corona treated (parameters: Power=0.3 kW; rotation speed 120 m/min; No of turns: 6) and then K bar (size 0) coated with a LPP solution (2% solid content in 80% MEK and 20% CHN). The wet film is dried at 80° C. for 120 s; the dry film thickness is about 60 nm. Then the dry film is exposed to linearly polarized collimated UVB light (25 mJ/cm²)

Then the sample is k bar (size 1) coated with a 30% solution of
  98.4% compound (XIII) as synthesized in example 1
  1.0% AD42
  0.5% AD184
  0.1% AD43
in a solvent mixture of 80% MEK and 20% CHN. The wet film is annealed and dried at 60° C. for 120 s and cross-linked under nitrogen with 1 J/cm² of un-polarized UVA light. After this treatment the film exhibited an uni-axial, uniform anisotropy without visible defects. The thickness of the cross linked polymer film turned out to be 1310 nm and exhibited a retardance of 135 nm at 550 nm.

Then the sample is k bar (size 2) coated with a 40% solution of
  94.4% compound (XIII) as synthesized in example 1
  4.0% Lumogen S750
  1.0% AD42
  0.5% AD138
  0.1% AD43
in MPK. The wet film is annealed and dried at 57° C. for 120 s and cross-linked under nitrogen with 1 J/cm² of un-polarized UVA light. After this treatment the film exhibits a cholesteric orientation with a reflection band centred at 615 nm and the width of the selective reflection band of a single cholesteric layer is about 40 nm. The layer appeared uniform without visible defects. The thickness of the cross linked cholesteric film turned out to be 2500 nm.

This combination of quarter wave plate and cholesteric film is well suited for circular polarizer applications in the region of the selective reflection.

Application/Example 6b

Cholesteric Circular Polarizer

A 40 micron thick hard coated TAC foil was corona treated (parameters: Power=0.3 kW; rotation speed 120 m/min; No of turns: 6) and then K bar (size 0) coated with a LPP solution (2% solid content in 80% MEK and 20% CHN). The wet film was dried at 80° C. for 120 s; the dry film thickness was about 60 nm. Then the dry film was exposed to linearly polarized collimated UVB light (25 mJ/cm²)

Then the sample was k bar (size 1) coated with a 30% formulation of
  95.4% compound (XIII) as synthesized in example 1
  4.0% AD282
  0.5% AD184
  0.1% AD43
in a solvent mixture of 80% DXG and 20% CHN. The wet film was annealed and dried at 60° C. for 120 s and cross-linked under air atmosphere with 1.5 J/cm² of un-polarized UVA light. After this treatment the film exhibited an uni-axial, uniform (=unpatterned, equal birefringent of the whole area of the film) anisotropy without visible defects. The thickness of the cross linked LCP film turned out to be 1310 nm. The film exhibited an optical retardance of 135 nm at 550 nm.

Then the sample was k bar (size 2) coated with a 40% solution of
  94.7% compound (XIII) as synthesized in example 1
  4.0% Lumogen S750
  4.0% AD282
  0.2% AD138
  0.1% AD43
in 80% MEK and 20% DXG2. The wet film was annealed and dried at 52° C. for 120 s and cross-linked under air atmosphere with 1.5 J/cm² of un-polarized UVA light. After this treatment the film exhibited a cholesteric orientation with a reflection band centred at 615 nm and the width of the selective reflection band of a single cholesteric layer was about 40 nm. The layer appeared uniform without visible defects. The thickness of the cross linked cholesteric film turned out to be 2500 nm.

This combination of quarter wave plate and cholesteric film is well suited for circular polarizer applications in the region of the selective reflection.

Application/Example 7

Security Element on PET Substrate

A 20 micron thick PET foil is corona treated (parameters: Power=0.3 kW; rotation speed 120 m/min; No of turns: 6) and then K bar (size 0) coated with a LPP solution (2% solid content in a solution of 80% MEK and 20% CHN). The wet film is dried at 80° C. for 120 s; the dry film thickness was about 60 nm. Then the dry film is first exposed to linearly polarized collimated UVB light (25 mJ/cm²; polarization azimuth angle φ=45° with respect to the orientation of the optical axis of the PET foil) through a mask and subsequently with 10 mJ/cm² without mask at a polarization azimuth angle of φ=−45°).

Then the sample is k bar (size 1) coated with a 30% solution of
  98.4% compound (XIII) as synthesized in example 1
  1.0% AD42
  0.5% AD184
  0.1% AD43
in a solvent mixture of 80% MEK and 20% CHN. The wet film is annealed and dried at 60° C. for 120 s and cross-linked under nitrogen with 1 J/cm² of un-polarized UVA light. After this treatment the film exhibits a patterned uni-axial anisotropy without visible defects. The thickness of the cross linked birefringent film turns out to be 1310 nm and exhibits a retardance of 135 nm at 550 nm. The optical axis of the birefringent film ss parallel oriented along the 45° azimuth angle (in the areas which were covered by the mask during the first exposure) and parallel oriented to −45° (with respect to the optical axis of the PET foil)

Then the sample is k bar (size 2) coated with a 40% solution of
  94.4% compound (XIII) as synthesized in example 1
  4.0% Lumogen S750

1.0% AD42
0.5% AD138
0.1% AD43 in MPK. The wet film is annealed and dried at 57° C. for 120 s and cross-linked under nitrogen with 1 J/cm$^2$ of un-polarized UVA light. After this treatment the film exhibited a cholesteric orientation with a reflection band centred at 615 nm. The layer appeared uniform without visible defects. The thickness of the cross linked cholesteric film turned out to be 2500 nm.

Finally, a black film is applied using a commercially available black lacquer (Rayoflex produced by Sun Chemicals) diluted with MEK. The adhesion to the cholesteric layer is excellent.

When observed through the PET foil with a polarizer this sample (comprising a patterned quarter wave plate and a cholesteric film) can be used as a second level security element showing a covered positive and a negative image respectively depending on the orientation of the polarizer. It also shows a first level colour shift effect, as a security feature.

Application/Example 8

A 20 micron thick PET foil is corona treated (parameters: Power=0.3 kW; rotation speed 120 m/min; No of turns: 6)
Then the sample is k bar (size 2) coated with a 40% solution of
94.4% compound (XIII) as synthesized in example 1
4.0% Lumogen S750
1.0% AD42
0.5% AD138
0.1% AD43 in MPK. The wet film is annealed and dried at 57° C. for 120 s and cross-linked under nitrogen with 1 J/cm$^2$ of un-polarized UVA light. After this treatment the film exhibits a cholesteric orientation with a reflection band centred at 620 nm and a width of the selective reflection band of a single cholesteric layer is about 40 nm. The layer appears uniform without visible defects. The thickness of the cross linked cholesteric film turns out to be 2500 nm. In addition the film shows exceptionally good adhesion to the PET foil. It is well suited for circular reflection filter applications in the region of the selective reflection.

Application/Example 9

Retarder on Glass Substrate

A glass substrate is spin coated with a LPP solution (2% solid content in 98% cyclopentnon). The wet film is dried at 180° C. for 10 s; the dry film thickness was about 60 nm. Then the dry film is exposed to linearly polarized collimated UVB light (120 mJ/cm$^2$).

Then the sample is spin coated with a 20% formulation of
67% compound B2 (as described in preparation example 1.2.1)
30% of LCP (1), 2,5-bis-[4-6-acryloyloxyhexyloxy)benzoyloxy]benzoic acid pentyl Ester, commercially available from ROLIC Technologies, Switzerland or prepared in analogy to Schemes 1, 2, 3, 4 of U.S. Pat. No. 5,593,617,
1.0% AD 42
1.0% AD18
1.0% AD43 in anisol. The wet film is annealed and dried at 180° C. for 10 s and crosslinked under nitrogen with 120 mJ/cm$^2$ of Hg-lamp. After this treatment the film exhibited an uni-axial, uniform orientation without visible defects. The thickness of the cross linked film turned out to be 802 nm. The film exhibits a retardance of 105 nm at 550 nm.

Application/Example 10

Retarder on Glass Substrate

Example 10 is identical to example 9 with the proviso that the compound B2 is replaced by compound B7 (as described in preparation example 1.2.1)

The thickness of the cross linked film turns out to be 790 nm. The film exhibits a retardance of 89 nm at 550 nm.

Application/Example 11

Retarder on Glass Substrate

A glass substrate is spin coated with a LPP solution (2% solid content in 98% cyclopenton). The wet film is dried at 180° C. for 4 min; the dry film thickness is about 60 nm. Then the dry film is exposed to linearly polarized collimated UVB light (200 mJ/cm$^2$).

Then the sample is spin coated with a 20% formulation of
87.9% of compound (XIII) as synthesized in example 1
10% of C2 as synthesized in example 1, table 2
1.0% Irgacure 369
1.0% Tinuvin 123
0.1% BHT in anisol. The wet film is annealed and dried at 60° C. for 120 s and crosslinked under nitrogen with 200 mJ/cm$^2$ of Hg-lamp. After this treatment the film exhibited an uni-axial, uniform orientation without visible defects. The thickness of the cross linked film turns out to be 710 nm. The film exhibits a retardance of 84 nm at 550 nm.

Application/Example 12

Retarder on Glass Substrate

A glass substrate is spin coated with a LPP solution (2% solid content in 98% cyclopentnon). The wet film is dried at 180° C. for 4 min; the dry film thickness is about 60 nm. Then the dry film is exposed to linearly polarized collimated UVB light (200 mJ/cm$^2$).

Then the sample is spin coated with a 20% formulation of
87.9% of compound (XIII) as synthesized in example 1
10% of B6 as synthesized in example 1, table 1
1.0% Irgacure 369
1.0% Tinuvin, 123
0.1% BHT in anisol. The wet film is annealed and dries at 73° C. for 120 s and crosslinks under nitrogen with 200 mJ/cm$^2$ of Hg-lamp. After this treatment the film exhibits an uni-axial, uniform orientation without visible defects. The thickness of the cross linked film turns out to be 760 nm. The film exhibited a retardance of 97 nm at 550 nm.

The invention claimed is:

1. Polymerisable liquid crystal compound having a liquid crystalline phase, which is represented by formula (IV):

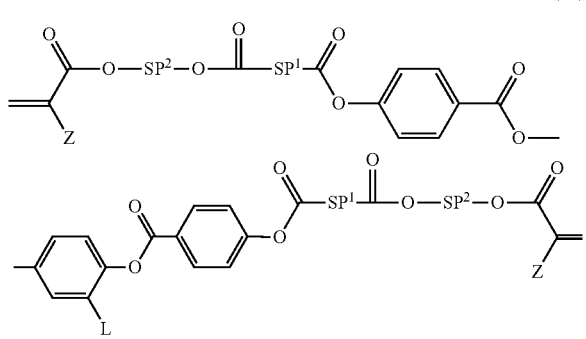

(IV)

wherein SP¹ represents a —CH═CH-group, —C≡C-group or a branched or unbranched $C_3$-$C_6$-alkylene group, SP² represents a substituted or unsubstituted spacer which is a branched or unbranched $C_1$-$C_{24}$-alkylene group, wherein one or more C-atom, —CH— or —CH$_2$-group is not replaced, or in which one or more C-atom, —CH— or —CH$_2$-group is replaced by a heteroatom or at least by a single replacing-group selected from the group consisting of —N═N—, —CO—CH═CH—, —CO—, —CH$_2$(CO)—, —SO—, —CH$_2$(SO)—, —SO$_2$—, —CH$_2$(SO$_2$)—, —COO—, —O(CO)—, —O(CO)—O—, —S—CO—, —CO—S—, —SOO—, —OSO—, —OCH$_2$—, —CH$_2$O—, —CH═CH— and —C≡C—; with the proviso that oxygen atoms are not directly linked to each other, and Z is hydrogen or methyl, and wherein:

L represents hydrogen, unbranched hydrocarbon group of 1 to 6 C-atoms, wherein one or more C-atom, —CH— or —CH$_2$—, is not replaced, or, is replaced by a heteroatom, which is —O—, —S—, —NH—, —N(CH$_3$)—, or is replaced by a replacing-group selected from the group consisting of —N═N—, —CO—C═C—, —CH(OH)—, —CO—, —SO—, —CH$_2$(SO)—, —SO$_2$—, —CH$_2$(SO$_2$)—, —COO—, —O(CO)—, —O(CO)—O—, —S—CO—, —CO—S—, —SOO—, —OSO—, —CH═CH— and —C≡C—, with the proviso that oxygen atoms are not directly linked to each other.

2. Compound according to claim 1, having an adhesion of >4.

3. A liquid crystalline composition comprising at least a compound as described in claim 1.

4. A method for the preparation of an unpatterned or patterned birefringent layer comprising polymerising a compound as described in claim 1.

5. A patterned or unpatterned birefringent layer comprising a compound as described in claim 1 that has been polymerised.

6. A method for the preparation of an optical or electro-optical component comprising preparing an optical or electro-optical component with a compound as described in claim 1.

7. An optical or electro-optical component comprising a compound as described in claim 1.

8. A method for the preparation of an unpatterned or patterned birefringent layer comprising preparing an unpatterned or patterned birefringent layer with a liquid crystalline composition as described in claim 3.

9. A patterned or unpatterned birefringent layer comprising a liquid crystalline composition as described in claim 3.

10. A method for the preparation of an optical or electro-optical component comprising preparing an optical or electro-optical component with a liquid crystalline composition as described in claim 3.

11. An optical or electro-optical component comprising a liquid crystalline composition as described in claim 3.

12. Compound according to claim 1, wherein SP¹ is —CH═CH-group or —C≡C-group.

* * * * *